US006440983B1

(12) United States Patent
Frank-Kollman

(10) Patent No.: US 6,440,983 B1
(45) Date of Patent: Aug. 27, 2002

(54) COMPOSITIONS AND METHODS FOR RELIEVING HEADACHE SYMPTOMS IN ASPIRIN-SENSITIVE HEADACHE SUFFERERS

(76) Inventor: Mary Theresa Frank-Kollman, 173 Egrets Way, Richmond Hill, GA (US) 31324

( * ) Notice: Subject to any disclaimer, the term of this patent is extended or adjusted under 35 U.S.C. 154(b) by 9 days.

(21) Appl. No.: 09/746,135

(22) Filed: Dec. 21, 2000

(51) Int. Cl.$^7$ .............................................. A01N 43/90
(52) U.S. Cl. ..................................................... 514/264
(58) Field of Search ................................ 514/520, 105, 514/253, 570, 101, 264

(56) References Cited

U.S. PATENT DOCUMENTS

| | | | | |
|---|---|---|---|---|
| 4,703,045 A | * | 10/1987 | Guinot ........................ | 514/159 |
| 4,783,465 A | * | 11/1988 | Sunshine et al. ............ | 514/255 |
| 5,696,165 A | * | 12/1997 | Armitage et al. ............ | 514/570 |
| 5,972,916 A | * | 10/1999 | Armellino et al. ........... | 514/165 |
| 6,077,539 A | * | 6/2000 | Plachetka et al. ............ | 424/474 |
| 6,218,192 B1 | * | 4/2001 | Altura et al. .................. | 436/79 |

OTHER PUBLICATIONS

Beubler, Wien Med Wochenschr, vol. 144, No. 5–6, pp. 100–1, 1994.*
Forbes et al, Clin Pharmacol Ther., vol. 49, No. 6, pp. 674–84, 1991.*
Virgilio Gallai, et al., "Magnesium Content of Mononuclear Blood Cells in Migraine Patients, " Headache, Mar. 1994, 160–165, vol. 34(3).
Katsuko Mishima, et al., "Platelet Ionized Magnesium, Cyclic AMP, and Cyclic GMP Levels in Migraine and Tension–Type Headache," Headache, Oct. 1997, 561–564, vol.37(9).
Alexander Mauskop, et al., "Intravenous Magnesium Sulfate Rapidly alleviates Headache of the Various Types," Headache, Mar. 1996, 154–160, vol.36(3).
M.F. McCarty, "Magnesium Taurate and Fish Oil for Prevention of Migraine, Medical Hypotheses," Dec. 1996, 461–466, vol.47(6), Pearson Professional Ltd., England.
Paolo Aloisi, et al., "Visual Evoked Potentials and Serum Magnesium Levels in Juvenile Migraine Patients," Headache, Jun. 1997, 383–385, vol.37(6).
Virgilio Gallai, et al., "Serum and Salvary Magnesium Levels in Migraine. Results in a Group of Juvenile Patients," Headache, Mar. 1992, 132–135, vol.32(3).
Miller, Tom, "The Role of Magnesium in The Prevention of Coronary Disease and Other Disorders," 21 pages, dated Jul. 23, 1997, dowloaded from http://www.execpc.com/~cc/tmiller.html, download date: Aug. 12, 2000.
"Migraine and Magnesium Deficiency," 4 pages, dated Feb. 19, 1999, downloaded from http://www.execpc.com/~magnesum/migraine.html, download date: (not available).
"Magnesium Abstracts," 20 pages, dated Jun. 28, 1999, downloaded from http://www.execpc.com/~cc/abstract.html, download date: Aug. 12, 2000.
St. Luke's Episcopal Hospital, "Acute and Chronic Sinusitis: What is Sinusitis?" 3 pages, (date not available), downloaded from http://www.sleh.com/FactSheets/fact–n03–sinus.html, download date: Aug. 20, 2000.
"Headache Coping Strategies Depend on The Cause," 3 pages, dated Aug. 14, 2000, downloaded from http://www.cnn.com/2000/HEALTH/08/14/headache.redux/index.html, download date: Aug. 14, 2000.
Diener, H.C., et al., "Antimigraine Drugs," 1 page, dated Jul. 1999, downloaded from http://www.ncbi.nlm.nih.gov:80/entrez/query.fcgi?CMD=Display&DB=PubMed, download date: Aug. 4, 2000.

* cited by examiner

Primary Examiner—James H. Reamer
(74) Attorney, Agent, or Firm—Gottlieb, Rackman & Reisman

(57) ABSTRACT

The treatment of migraine and/or cluster headaches in human beings in need of such treatment includes oral administration of a composition containing acetaminophen, ibuprofen, caffeine and magnesium as the active ingredients. The inclusion of an additional active ingredient, guaifenesin, further provides treatment for severe sinus headaches. Compositions and methods for alleviating the symptoms of these headache conditions are disclosed.

16 Claims, No Drawings

COMPOSITIONS AND METHODS FOR RELIEVING HEADACHE SYMPTOMS IN ASPIRIN-SENSITIVE HEADACHE SUFFERERS

TECHNICAL FIELD

The present invention relates broadly to the field of healthcare, and in particular, to the treatment of severe headaches in human beings. More specifically, this invention relates to compositions and methods for providing relief from the symptoms of migraine headaches and/or cluster headaches and/or headaches related to sinus congestion, in affected individuals who also have a low tolerance for aspirin due to digestive disorders.

BACKGROUND OF THE INVENTION

Migraine is a particularly painful headache, which recurs and can be physically debilitating to sufferers. In many respects, cluster headaches are similar to migraine headaches, and all references herein to migraine and/or migraine headaches shall be considered as also including, and as references to, cluster headaches. There is no single cause or remedy for migraine headaches, and the incidence of migraine appears to be increasing in the general population. Although sufferers, on average, experience only one attack per month, each attack can last between four and seventy-two hours. In some cases, sufferers experience a pre-onset "warning" which may indicate that a migraine is imminent, and which may be termed an "aura." An "aura" is a disruption of brain function characterized by visual disturbances like flashing lights and blurred vision. These "disruptions" occur twenty to thirty minutes before an attack. About twenty percent of migraine suffers experience "aura" symptoms. Other attacks can be preceded by a "prodrome" several hours before the onset of a migraine. These "prodrome" symptoms may include, but are not limited to, fatigue, yawning, sensory sensitivity, mood changes, and food cravings.

Prescription medications have previously been developed to alleviate the severity of migraine pain, but prescription migraine medications generally contain some type of narcotic, which, over time, may become addictive. Although over-the-counter remedies also exist, marketed under the EXCEDRIN® and ADVIL® brands, the EXCEDRIN® Migraine Formula contains aspirin, acetaminophen, and caffeine as its active ingredients, while the only active ingredient of the ADVIL® Migraine product is ibuprofen. Many migraine sufferers cannot take aspirin, due to digestive disorders, such as acid reflux disease, ulcers, and acid indigestion, and for many such sufferers, ibuprofen alone is not sufficient to lessen the pain or to reduce it to a manageable level. It would therefore be desirable to provide a non-prescription remedy which alleviates migraine symptoms in a manner not accomplished by the currently available "over-the-counter" remedies.

Sinus congestion (sinusitis) is also a cause of severe headaches, which can produce some of the same symptoms as migraine, such as nausea, vomiting, severe pain, and sensitivity to light, and severe sinus headache sufferers can sometimes experience "aura" and/or "prodrome" symptoms as well. Current over-the-counter remedies specifically formulated to treat severe sinus headaches contain antihistamines and decongestants, in addition to analgesics. However, antihistamines provide relief only if sinusitis is caused by an allergy, and although a decongestant can be helpful, it also can worsen the symptoms if the sinusitis does not result from infection or is acute, because a decongestant will dry up the mucous membranes and can cause further impaction of the sinus cavities.

In the case of chronic sinusitis, an expectorant may be more helpful by liquefying the mucous and allowing the sinus cavities to drain, thereby relieving the pressure contributing to severe sinus headache. Expectorants are commonly used in over-the-counter medicines, but primarily in the treatment of coughs and chest congestion, not for sinus pain relief.

No currently available over-the-counter remedy provides for an expectorant combined with relief from the migraine-like symptoms of severe sinus headache, and it would therefore be desirable to provide a non-narcotic, non-prescription remedy which alleviates those symptoms, without the use of a decongestant or an antihistamine, in a manner not accomplished by the currently available over-the-counter remedies.

Recent research and clinical trials suggest that the mineral magnesium can provide some relief from migraine symptoms, at least in sufferers who have a measurable magnesium deficiency. A large percentage of the population of sufferers may indeed show this deficiency, which may contribute to migraine onset, and sufferers of severe sinus headache may exhibit this deficiency as well. Thus, an over-the-counter remedy for cluster and/or migraine headache should address potential magnesium deficiency and sensitivity to aspirin, but should also be strong enough to provide relief, and an over-the-counter remedy for severe sinus headache should address congested and impacted sinus cavities as well. The present invention is directed to meeting one or more of the above-stated desirable objectives.

SUMMARY OF THE INVENTION

The invention provides compositions, in pharmaceutically effective forms and amounts, as well as methods, for treating both migraine/cluster headaches and severe sinus headaches, in human beings in need of such treatment.

In accordance with one aspect of the invention, a migraine/cluster headache remedy is provided by combining a pain-masking analgesic (such as acetaminophen), a non-steroidal anti-inflammatory agent (such as ibuprofen), a central nervous system stimulant (such as caffeine), and magnesium.

A feature of this aspect of the invention is that it provides pain relief through the combination of acetaminophen and ibuprofen, neither of which contains any aspirin.

Another feature of this aspect of the invention is the inclusion of the mineral magnesium as an active ingredient to remedy severe headache. This mineral ingredient advantageously addresses magnesium deficiency and its link to migraine/cluster headache cause.

In accordance with another aspect of the invention, a severe sinus headache remedy is provided by combining an expectorant (such as guaifenesin) with a pain-masking analgesic (such as acetaminophen), a nonsteroidal anti-inflammatory agent (such as ibuprofen), a central nervous system stimulant (such as caffeine), and magnesium.

A feature of this aspect of the invention, in addition to the features set forth above, is that it provides an expectorant (guaifenesin) as a means for inducing drainage of mucous secretions from the sinus passageways, without using a decongestant or antihistamine.

DETAILED DESCRIPTION OF THE PREFERRED EMBODIMENT

In accordance with a first embodiment of the invention, the combination of four active ingredients namely, acetaminophen, ibuprofen, caffeine and magnesium, in a pharmaceutically-acceptable form and in therapeutically-effective dosage, provides strong pain relief for sufferers of migraine/cluster headaches. Generally, these ingredients are utilized in the following amounts for a single dose: 100–500 mg. of acetaminophen, 100–500 mg. of ibuprofen, 25–150 mg. of caffeine and 100–500 mg. of magnesium. Preferably, the following amounts of these ingredients are used: 200–400 mg. of acetaminophen, 200–400 mg. of ibuprofen, 50–100 mg. of caffeine and 150–400 mg. of magnesium. Most preferably, the inventive composition comprises the following amounts of these ingredients: approximately 250 mg. of acetaminophen, approximately 250 mg. of ibuprofen, approximately 75 mg. of caffeine and approximately 250 mg. of magnesium.

In accordance with a second embodiment of the invention, the combination of five active ingredients, namely, guaifenesin, acetaminophen, ibuprofen, caffeine and magnesium, in a pharmaceutically-acceptable form and in a therapeutically-effective dosage, provides strong pain relief as well as sinus drainage for sufferers of severe sinus headaches. Generally, these ingredients are utilized in the following amounts for a single dose: 200–400 mg. of guaifenesin, 100–500 mg. of acetaminophen, 100–500 mg. of ibuprofen, 25–150 mg. of caffeine and 100–500 mg. of magnesium. Preferably, the following amounts of these ingredients are used: 300–400 mg. of guaifenesin, 200–400 mg. of acetaminophen, 200–400 mg. of ibuprofen, 50–100 mg. of caffeine and 150–400 mg. of magnesium. Most preferably, the inventive composition comprises the following amounts of these ingredients: approximately 400 mg. of guaifenesin, approximately 250 mg. of acetaminophen, approximately 250 mg. of ibuprofen, approximately 75 mg. of caffeine and approximately 250 mg. of magnesium.

Each embodiment of the invention further encompasses methods for treating human beings suffering from these types of headaches, comprising administering the combinations of ingredients described above together with a pharmaceutically-acceptable carrier.

Guaifenesin, acetaminophen, ibuprofen, caffeine, and magnesium are all in the public domain. The chemical name for acetaminophen is 4'-hydroxyacetanilide, having the empirical formula $C_8H_9NO_2$. Ibuprofen is known chemically as (35)-2-(p-isobutylphenyl)propionic acid, with the formula $C_{13}H_{18}O_2$, while guaifenesin has the chemical name 3-(2-methoxphenoxy)-1,2-propanediol, and has the formula $C_{10}H_{14}O_4$. The empirical formula for caffeine is $C_8H_{10}N_4O_2$.

Acetaminophen, ibuprofen, and guaifenesin can all be procured in tablet form from Aceto Corporation of Lake Success, N.Y. Magnesium can be obtained easily, in either tablet or capsule form, from a number of sources including, but not limited to, Twinlab Corporation of Hauppauge, N.Y., Weider Nutrition International, Inc. of Salt Lake City, Utah (under the Schiff® brand), or even through the Internet from VitaminShoppe.com, Inc. at http://www.vitaminshoppe.com. Caffeine is available in tablet form from SmithKline Beecham of Philadelphia, Pa. It can also be isolated from tea relatively simply, in a well-known manner, as demonstrated in the experiments conducted annually as an exercise by the students in the Department of Chemistry at Okanagan University College, located in Kelowna, British Columbia, Canada. As reported (at http:www.sci.ouc.bc./chem/faculty/neeland2.html on the Internet), these experiments were modified to a micro scale, using the contents of only one tea bag, which yielded approximately 10–12 mg. of caffeine.

The following examples illustrate the manner in which the active ingredients may be combined, and how the combination can be administered to a sufferer in an oral fashion, utilizing a pharmaceutically-acceptable carrier which, in some cases, can constitute a beverage or a foodstuff. Examples 1–5 describe the migraine/cluster headache remedy while Examples 6–10 refer to the severe sinus headache remedy.

EXAMPLE 1

One 250 mg. tablet of acetaminophen, two and one-half 100 mg. tablets of ibuprofen, three-quarters of one 100 mg. tablet of caffeine, and two and one-half 100 mg. tablets of magnesium, are each crushed separately into a powder. All of the powders are then combined and are placed into a conventional gelatin capsule in a known manner, which acts as a pharmaceutically-acceptable carrier, and can be ingested by those accustomed to swallowing pills.

EXAMPLE 2

The same ingredients and carrier are used as in Example 1, except that 75 mg. of powdered caffeine extracted from tea bags is used, instead of using powdered caffeine obtained from a commercially-available tablet.

EXAMPLE 3

The same ingredients are used as in Examples 1 or 2, except that instead of placing the powdered ingredients into a gelatin capsule, all of the powdered ingredients are placed in the center of a one-half dollar size piece of soft bread. The bread is then rolled into a ball with the powder inside, and is either chewed or swallowed whole with at least 8 oz. of water.

EXAMPLE 4

The same ingredients are used as in Examples 1 or 2, except that all of the powdered ingredients are dissolved by vigorous stirring in at least 8 oz. of chocolate milk for easier ingestion.

EXAMPLE 5

The same ingredients are used as in Examples 1, 2 or 3, except that the powdered caffeine is omitted entirely, and all of the remaining powdered ingredients are instead dissolved by stirring into at least 12 oz. of warm or cold caffeinated tea, or into at least 24 oz. of a caffeinated diet cola beverage.

EXAMPLE 6

Two 200 mg. tablets of guaifenesin, one 250 mg. tablet of acetaminophen, two and one-half 100 mg. tablets of ibuprofen, three-quarters of one 100 mg. tablet of caffeine, and two and one-half 100 mg. tablets of magnesium, are each crushed separately into a powder. All of the powders are then combined and are placed into a conventional gelatin capsule in a known manner, which acts as a pharmaceutically-acceptable carrier, and can be ingested by those accustomed to swallowing pills.

EXAMPLE 7

The same ingredients and carrier are used as in Example 6, except that 75 mg. of powdered caffeine extracted from tea bags is used, instead of using powdered caffeine obtained from a commercially-available tablet.

EXAMPLE 8

The same ingredients are used as in Examples 6 or 7, except that instead of placing the powdered ingredients into a gelatin capsule, all of the powdered ingredients are placed in the center of a one-half dollar size piece of soft bread. The bread is then rolled into a ball with the powder inside, and is either chewed or swallowed whole with at least 8 oz. of water.

EXAMPLE 9

The same ingredients are used as in Examples 6 or 7, except that all of the powdered ingredients are dissolved by vigorous stirring in at least 8 oz. of chocolate milk for easier ingestion.

EXAMPLE 10

The same ingredients are used as in Examples 6, 7 or 8, except that the powdered caffeine is omitted entirely, and all of the remaining powdered ingredients are instead dissolved by stirring into at least 12 oz. of warm or cold caffeinated tea, or into at least 24 oz. of a caffeinated diet cola beverage.

Each of the foregoing recipes constitutes a single unit dosage of the associated composition, and should be ingested orally at the first indication of the onset of a severe sinus headache. Experimental results which demonstrate the efficacy of these compositions are set forth below.

The composition of the first embodiment of the invention was administered to five subjects, each on one occasion, at the onset of a severe headache. Two of the subjects had a prior history of aspirin sensitivity (resulting from ulcers and/or acid reflux disease), and one of those two subjects was also suffering from nausea as well as "aura" symptoms. That subject experienced about 25% relief within about fifteen minutes of ingesting the composition; the other subject with a history of aspirin sensitivity experienced more than 50% pain reduction within about the same time period. Neither of these two subjects experienced any stomach pain as a result of taking the remedy. Of the remaining three subjects (who had no history of aspirin sensitivity), two experienced about 50% relief within about twenty minutes after ingesting the composition, and one of those two achieved complete relief within about ten additional minutes. The fifth subject experienced complete relief within about one hour after ingesting the inventive composition, although for that subject the composition was supplemented with an ice pack under the neck.

The composition of the first embodiment of the invention was also self-administered on ten separate occasions, and complete relief from the severe headache symptoms was achieved on eight of those occasions, while at least 50% relief was experienced on the other two occasions. The relief was perceived in as little as about thirty minutes and as much as about forty-five minutes.

The composition of the second embodiment of the invention was administered to five subjects, each on one occasion, all of whom were complaining of severe sinus headache. All five subjects were suffering from nausea, and three were complaining of pressure and "congestion in their head" associated with such headaches. Two of the five subjects were simultaneously suffering from sensitivity to light and noise.

One of the five subjects experienced complete relief within about thirty minutes of ingesting the composition, one experienced about 75% relief within about thirty minutes, one experienced about 50% relief after about one hour, and one experienced approximately 25% relief within forty-five minutes, although in the latter case crackers were consumed together with the inventive composition. One subject experienced no relief at all. The subject who experienced complete relief had ingested the remedy dissolved in either diet cola or warm tea (e.g., the composition of Example 10); in other words, in this case the caffeine was not introduced into the composition in powdered form. Two of the subjects had a prior history of aspirin sensitivity (resulting from ulcers and/or acid reflux disease), but neither experienced any stomach pain as a result of taking the composition.

The composition of the second embodiment of the invention (formulated as in Example 10) was also self-administered on four occasions, and complete relief from the sinus headache symptoms (including the nausea and the feeling of pressure and "congestion in the head") was achieved on two occasions, while more than 50% relief was experienced on the two other occasions. The relief was perceived in as little as about twenty minutes and as much as about forty-five minutes. By contrast, when the currently available over-the-counter sinus headache remedies (which include a decongestant as an active ingredient) were self-administered, these over-the-counter remedies actually made the headache worse.

The second embodiment of the invention allows for the probability that sinus congestion causes pain due to increased pressure in the sinus cavities, and it does so by including an expectorant as an active ingredient, which allows the mucous to liquefy and drain, thereby reducing the congestion. Both embodiments of the invention also allow also for the possibility that magnesium deficiency is a contributing factor in the cause of migraine/cluster headache and/or severe sinus headache, and they provide relief by including magnesium as an active ingredient. The inclusion of magnesium may also contribute to the lack of any stomach pain in the subjects who had a history of aspirin sensitivity because magnesium is sometimes used as an active ingredient in chewable over-the-counter stomach acid relief medications. One of the complications often experienced by those using such a magnesium acid reducer (such as the MYLANTA® brand product) is that it can cause diarrhea. However, none of the subjects experienced any diarrhea as a result of using any of the compositions of this invention.

While there has been described what are at present considered to be the preferred embodiments of the present invention, it will be apparent to those skilled in the art that the embodiments described herein are by way of illustration and not of limitation, and that various changes and modifications may be made therein without departing from the true spirit and scope of the present invention, as set forth in the appended claims.

What is claimed is:

1. A composition which elicits a therapeutic response in a human comprising effective amounts of acetaminophen, ibuprofen, caffeine and magnesium, incorporated into a pharmaceutically acceptable carrier, wherein said composition is substantially free of aspirin.

2. A pharmaceutical composition for oral administration comprising, in combination, a therapeutically effective amount of acetaminophen, a therapeutically effective amount of ibuprofen, a therapeutically effective amount of caffeine, and a therapeutically effective amount of magnesium, said combination being incorporated into a pharmaceutically acceptable carrier, wherein said composition is substantially free of aspirin.

3. An orally-administered pharmaceutical composition for treatment of a condition selected from the group consisting of migraine headache and cluster headache in a human in need of such treatment, said composition comprising, in combination, a therapeutically effective amount of acetaminophen, a therapeutically effective amount of ibuprofen, a therapeutically effective amount of caffeine, and a therapeutically effective amount of magnesium, said combination being incorporated into a pharmaceutically acceptable carrier, wherein said composition is substantially free of aspirin.

4. The composition of claims 1, 2 or 3 wherein said effective amount of acetaminophen is 100–500 mg. per unit dosage of said composition, said effective amount of ibuprofen is 100–500 mg. per unit dosage of said composition, said effective amount of caffeine is 25–150 mg. per unit dosage of said composition, and said effective amount of magnesium is 100–500 mg. per unit dosage of said composition.

5. The composition of claim 4 wherein said effective amount of acetaminophen is 250 mg. per unit dosage of said composition, said effective amount of ibuprofen is 250 mg. per unit dosage of said composition, said effective amount of caffeine is 75 mg. per unit dosage of said composition, and said effective amount of magnesium is 250 mg. per unit dosage of said composition.

6. The composition of claim 5 wherein said pharmaceutically acceptable carrier is selected from the group consisting of gelatin capsules, beverages and foodstuffs.

7. A method for the treatment in a human subject of a condition selected from the group consisting of migraine headache and cluster headache, said method comprising the step of orally administering to a subject in need of such treatment a therapeutically effective amount of a composition according to claim 6.

8. A method for the treatment in a human subject of a condition selected from the group consisting of migraine headache and cluster headache, said method comprising the step of orally administering to a subject in need of such treatment a therapeutically effective amount of a composition according to claim 1.

9. A composition which elicits a therapeutic response in a human comprising effective amounts of guaifenesin, acetaminophen, ibuprofen, caffeine and magnesium, incorporated into a pharmaceutically acceptable carrier, wherein said composition is substantially free of aspirin.

10. A pharmaceutical composition for oral administration comprising, in combination, a therapeutically effective amount of guaifenesin, a therapeutically effective amount of acetaminophen, a therapeutically effective amount of ibuprofen, a therapeutically effective amount of caffeine, and a therapeutically effective amount of magnesium, said combination being incorporated into a pharmaceutically acceptable carrier, wherein said composition is substantially free of aspirin.

11. An orally-administered pharmaceutical composition for treatment of severe sinus headache in a human in need of such treatment, said composition comprising, in combination, a therapeutically effective amount of guaifenesin, a therapeutically effective amount of acetaminophen, a therapeutically effective amount of ibuprofen, a therapeutically effective amount of caffeine, and a therapeutically effective amount of magnesium, said combination being incorporated into a pharmaceutically acceptable carrier, wherein said composition is substantially free of aspirin.

12. The composition of claims 9, 10 or 11 wherein said effective amount of guaifenesin is 200–400 mg. per unit dosage of said composition, said effective amount of acetaminophen is 100–500 mg. per unit dosage of said composition, said effective amount of ibuprofen is 100–500 mg. per unit dosage of said composition, said effective amount of caffeine is 25–150 mg. per unit dosage of said composition, and said effective amount of magnesium is 100–500 mg. per unit dosage of said composition.

13. The composition of claim 12 wherein said effective amount of guaifenesin is 400 mg. per unit dosage of said composition, said effective amount of acetaminophen is 250 mg. per unit dosage of said composition, said effective amount of ibuprofen is 250 mg. per unit dosage of said composition, said effective amount of caffeine is 75 mg. per unit dosage of said composition, and said effective amount of magnesium is 250 mg. per unit dosage of said composition.

14. The composition of claim 13 wherein said pharmaceutically acceptable carrier is selected from the group consisting of gelatin capsules, beverages and foodstuffs.

15. A method for the treatment in a human subject of severe sinus headache, said method comprising the step of orally administering to a subject in need of such treatment a therapeutically effective amount of a composition according to claim 14.

16. A method for the treatment in a human subject of severe sinus headache, said method comprising the step of orally administering to a subject in need of such treatment a therapeutically effective amount of a composition according to claim 9.

\* \* \* \* \*